United States Patent
Andre et al.

(10) Patent No.: US 9,975,825 B1
(45) Date of Patent: May 22, 2018

(54) PROCESS FOR THE PURIFICATION OF PENTAFLUOROETHANE

(71) Applicant: ARKEMA FRANCE, Colombes (FR)

(72) Inventors: David Andre, Brignais (FR); Abdelatif Baba-Ahmed, Saint-Fons (FR)

(73) Assignee: ARKEMA FRANCE, Colombes (FR)

( * ) Notice: Subject to any disclaimer, the term of this patent is extended or adjusted under 35 U.S.C. 154(b) by 0 days. days.

(21) Appl. No.: 15/566,074

(22) PCT Filed: Apr. 11, 2016

(86) PCT No.: PCT/EP2016/057882
§ 371 (c)(1),
(2) Date: Oct. 12, 2017

(87) PCT Pub. No.: WO2016/166045
PCT Pub. Date: Oct. 20, 2016

(30) Foreign Application Priority Data

Apr. 14, 2015 (FR) ..................................... 15 53226

(51) Int. Cl.
*C07C 17/386* (2006.01)
*C07C 17/00* (2006.01)

(52) U.S. Cl.
CPC ................................. *C07C 17/386* (2013.01)

(58) Field of Classification Search
CPC ........ C07C 17/386; C07C 19/12; C07C 19/08
See application file for complete search history.

(56) References Cited

U.S. PATENT DOCUMENTS

| | | |
|---|---|---|
| 3,113,079 A | 12/1963 | Bergeron et al. |
| 3,505,233 A | 4/1970 | Clark et al. |
| 3,689,372 A | 9/1972 | Sugano et al. |
| 5,207,876 A | 5/1993 | Berg et al. |
| 5,346,595 A | 9/1994 | Clemmer et al. |
| 5,919,340 A | 7/1999 | Kohno et al. |
| 6,039,845 A | 3/2000 | Bertocchio et al. |
| 2002/0040172 A1 | 4/2002 | Guiraud et al. |

FOREIGN PATENT DOCUMENTS

| | | |
|---|---|---|
| EP | 0 508 631 A1 | 10/1992 |
| EP | 0 669 302 A1 | 8/1995 |
| EP | 0 778 254 A1 | 6/1997 |
| FR | 2 215 407 A1 | 8/1974 |
| FR | 2 730 228 A1 | 8/1996 |
| FR | 2 758 137 A1 | 7/1998 |
| WO | WO 95/21148 A1 | 8/1995 |
| WO | WO 96/06063 A1 | 2/1996 |

OTHER PUBLICATIONS

International Search Report (PCT/ISA/210) dated Jun. 14, 2016, by the European Patent Office as the International Searching Authority for International Application No. PCT/EP2016/057882.
Written Opinion (PCT/ISA/237) dated Jun. 14, 2016, by the European Patent Office as the International Searching Authority for International Application No. PCT/EP2016/057882.

*Primary Examiner* — Jafar Parsa

(74) *Attorney, Agent, or Firm* — Buchanan Ingersoll & Rooney P.C.

(57) ABSTRACT

The invention relates to a process for the purification of pentafluoroethane (R125) containing chloropentafluoroethane (R115). The mixture to be purified is subjected to an extractive distillation, the extractant being selected from dimethylformamide (DMF), dioxane, dimethylsulphoxide (DMSO) and diethylsulphoxide (DESO).

8 Claims, No Drawings

PROCESS FOR THE PURIFICATION OF PENTAFLUOROETHANE

FIELD OF THE INVENTION

The invention relates to the purification of pentafluoroethane (R125) containing chloropentafluoroethane (R115) and more particularly relates to a purification process in which the R115 is removed by extractive distillation.

TECHNICAL BACKGROUND

Pentafluoroethane is one of the possible substitutes for chlorofluorocarbons (CFCs) to which the Montreal protocol applies and which are characterized by an exceptionally long life span enabling them to reach the upper layers of the atmosphere and thus to contribute under the influence of UV radiation to the destruction of the ozone layer. It is therefore obvious that their substitutes must contain only traces of these CFCs, depending on the various processes for obtaining them.

The substitutes are generally obtained either by suitable fluorination methods which are not highly selective and can generate perhalogenated compounds of the CFC type by disproportionation, i.e. from CFCs themselves by reduction methods, in practice by hydrogenolysis reactions. It is in this way that pentafluoroethane (R125) can be prepared by fluorination of perchloroethylene or intermediate fluorination products thereof such as dichlorotrifluoroethane (R123) and chlorotetrafluoroethane (R124), or by hydrogenolysis of chloropentafluoroethane (R115). In both cases, the R125 produced contains significant quantities of R115 that it is advisable to remove as completely as possible, R115 being a CFC.

However, the existence of an R115/R125 azeotrope containing 21% by weight R115 (see U.S. Pat. No. 3,505,233) with a boiling point (−48.5° C. under 1.013 bar) very close to that of R125 (−481° C.) makes the complete separation of R115 and R125 by distillation practically impossible unless technically complex processes are used such as azeotropic distillation at different pressures as described in U.S. Pat. No. 5,346,595. The removal of R115 from R125 can therefore only be done by a chemical route or by physical methods involving an entrainer.

In patent application EP 0 508 631 which describes the production of hydrofluorocarbons (HFCs) by chemical reduction in liquid phase of chlorinated, brominated or iodinated compounds with a metal hydride or a complex of such a hydride, it is indicated that this process can be useful for purifying certain HFCs such as pentafluoroethane. To the same end, the Japanese patent application (Kokai) published under No, 2001414/90 uses metallic redox pairs in a solvent medium. Other techniques such as that described in the Journal of Fluorine Chemistry, 1991 vol. 55, p. 105-107, use organic reducing agents such as ammonium formate in a DMF medium and in the presence of ammonium persulphate.

These processes which require reagents that are difficult to handle (metal hydrides) or likely to pose effluent problems, are not very compatible with the industrial production of R125 in significant tonnages.

For the industrial production of R125, the extractive distillation technique appears to be the ideal process for removing the residual R115.

In an extractive distillation process, separation of the constituents of a binary mixture is carried out using a column called an extraction column comprising successively, from the boiler to the top, three sections, one for stripping, the second for absorption and the third for recovery.

The binary mixture to be fractionated is injected at the top of the stripping section while the entrainer acting as a selective solvent or extractant is introduced at the top of the absorption section so as to travel in the liquid state from its point of introduction to the boiler.

The third section called recovery section serves to separate by distillation the least absorbed constituent, from traces of solvent entrained under the effect of the non zero vapour pressure thereof.

Document EP 0 669 302 describes a process for the purification of pentafluoroethane containing chloropentafluoroethane by extractive distillation, the extractant being a C5 to C8 alkane or a cycloalkane.

Document FR 2 758 137 describes a process for the purification of pentafluoroethane containing chloropentafluoroethane by extractive distillation, the extractant being a C5 to C8 perfluoroalkyl halide.

Document FR 2 730 228 describes a process for the purification of pentafluoroethane containing chloropentafluoroethane by extractive distillation, the extractant being perchloroethylene.

Document WO 96/06063 describes a process for the purification of pentafluoroethane comprising bringing pentafluoroethane into contact with a liquid polar organic compound comprising at least one nitrogen atom and/or an oxygen atom.

Certain of these extractants do not satisfy the conditions imposed in terms of environmental requirements.

Extractants have been found making it possible to satisfy environmental requirements and having an improved selectivity and/or capacity.

SUMMARY OF THE INVENTION

Firstly, the invention relates to a process for the purification of pentafluoroethane containing chloropentafluoroethane by extractive distillation, said process comprising the use of an extractant selected from dimethylformamide, dioxane, dimethylsulphoxide and diethylsulphoxide.

According to an embodiment, the extractant is selected from dimethylsulphoxide and diethylsulphoxide.

Preferably, the distillation is carried out under a pressure ranging from pressure atmospheric to 20 bars.

According to an embodiment of the invention, the pentafluoroethane/chloropentafluoroethane molar ratio before distillation ranges from 2 to 99.

According to an embodiment of the invention, the pentafluoroethane/chloropentafluoroethane molar ratio after distillation ranges from 5 to 99999.

According to an embodiment of the invention, the mixture containing pentafluoroethane and chloropentafluoroethane to be purified originates from the fluorination reaction of perchloroethylene or an intermediate fluorination product of said perchloroethylene.

According to an embodiment of the invention, the intermediate fluorination product of said perchloroethylene is selected from dichlorotrifluoroethane or chlorotetrafluoroethane.

According to an embodiment of the invention, the mixture containing pentafluoroethane and chloropentafluoroethane to be purified originates from the hydrogenolysis reaction of chloropentafluoroethane.

The process according to the invention is simple to implement, particularly on an industrial scale.

The process according to the invention makes it possible to recover pentafluoroethane with a greater purity.

The process according to the invention uses solvents having a lower toxicity and thus having a lesser impact on the environment.

The process according to the invention has an improved selectivity and/or an improved capacity.

DESCRIPTION OF EMBODIMENTS OF THE INVENTION

The invention is now described in more detail and non limitatively in the description which follows.

The present invention proposes a process for the purification of a pentafluoroethane (R125) containing chloropentafluoroethane (R115) by extractive distillation, said process comprising the use of an extractant selected from dimethylformamide (DMF), dioxane, dimethylsulphoxide (DMSO) and diethylsulphoxide (DESO).

The dioxane can be 1,4-dioxane, 1,3-dioxane or 1,2-dioxane. Preferably, the dioxane is 1,4-dioxane.

According to an embodiment of the invention, the extractant is selected from dioxane, dimethylsulphoxide and diethylsulphoxide.

According to an embodiment of the invention, the extractant is selected from dimethylsulphoxide and diethylsulphoxide.

According to an embodiment of the invention, the pentafluoroethane to be purified comprises in particular pentafluoroethane and chloropentafluoroethane.

According to an embodiment, the R125/R115 molar ratio before distillation ranges from 2 to 99.

According to an embodiment, the R125/R115 molar ratio after distillation ranges from 5 to 99999.

According to an embodiment, the purified pentafluoroethane comprises less than 10 ppm by weight of R115.

Preferably, the process according to the invention is carried out without the presence of metal hydrides or ammonium salts.

The process according to the invention can be implemented according to the well-known principles of extractive distillation. The operation can be carried out in an extractive distillation column in which the R125-R115 mixture to be separated is injected at a point situated at the top of the stripping section. The extractant is introduced into the column at a point situated at the top of the absorption section; it travels in the liquid state from its point of introduction to the boiler.

The diameter and the number of stages of the extractive distillation column, the reflux ratio and the optimum temperatures and pressures can be easily calculated by a person skilled in the art from the characteristic data for the individual constituents and for their mixtures (relative volatilities, vapour pressures and physical constants).

According to an embodiment of the invention, the distillation is carried out under a pressure ranging from atmospheric pressure to 20 bars absolute.

According to an embodiment of the invention, the distillation is carried out at a temperature ranging from −50° C. to 250° C., preferably from −10° C. to 200° C., more preferably from 5° C. to 150° C.

During the purification process according to the invention, the extractant selectively absorbs the R125.

In this embodiment, the extractant then preferably has a separation factor F at 25° C., as defined below, greater than 2, preferably greater than 3, more preferably greater than 4.

The separation factor (F) is defined as follows:

$$F = \frac{\gamma(R115)}{\gamma(R125)} \times \frac{P(R115)}{P(R125)}$$

where γ(R125) represents the activity coefficient of compound R125 in the solvent considered at infinite dilution.

γ(R115) represents the activity coefficient of compound R115 in the solvent considered at infinite dilution.

P(R125) represents the vapour pressure of compound R125 at the temperature considered.

P(R115) represents the vapour pressure of compound R115 at the temperature considered.

The ratio P(R125)/P(R115) corresponds to the relative volatility of R125 with respect to R115.

And as in the specific case of the present invention, the ratio of the vapour pressures is constant whatever the extraction solvent used, we can considerer a simplified separation factor F' or selectivity factor S defined by:

$$F' = \frac{\gamma(R115)}{\gamma(R125)}$$

The values of the activity coefficients of the compounds i (i is R125 or R115), $\gamma_i$, are calculated according to the relationship:

$$\ln \gamma_j = (\mu_j^i - \mu_j^p)/RT,$$

where $\mu_j^i$ corresponds to the chemical potential of compound i at infinite dilution in the solvent considered, and $\mu_j^p$ correspond with the chemical potential of pure compound i, and R is the perfect gas constant, and T is the temperature.

The activity coefficient and the vapour pressure are well-known data and accessible to a person skilled in the art.

The capacity of a solvent is defined by the inverse of the activity coefficient of the solute in the solvent at infinite dilution.

According to an embodiment of the invention, the purification process according to the invention comprises moreover a subsequent stage of separation of the extraction solvent and of the compound R125 as is known to a person skilled in the art and described for example in the document EP 778254. A solvent regeneration column makes it possible to separate the solvent/R125 mixture according to their difference in boiling point. The solvent recovered can be reused for the extractive distillation.

The selectivity and the capacity of different solvents are indicated in the following Table 1:

TABLE 1

| capacity and selectivity of the solvents | | |
|---|---|---|
| Solvent | Simplified separation factor (F') = selectivity S | Capacity |
| Acetonitrile | 6.31 | 0.3 |
| THF | 7.64 | 2.09 |
| Hexane | 0.63 | 0.18 |
| Acetone | 9.86 | 1.29 |
| DMF | 16.05 | 1.63 |
| 1,4-dioxane | 8.86 | 1.12 |
| dimethylsulphoxide | 30.08 | 0.73 |
| Diethylsulphoxide | 22.72 | 1.94 |

The data of Table 1 show that except for hexane, all these solvents have good extraction characteristics.

It is shown here that new solvents such as DMF, 1,4-dioxane, DMSO and DESO give very good results in terms of selectivity and/or capacity. These 4 solvents present an excellent choice in terms of performances for the extractive distillation. Moreover, these solvents are not, or are not very, harmful to the environment.

DMSO and DESO have excellent selectivities, of 30.08 and 22.72 respectively.

On the other hand, other solvents conventionally used, such as acetonitrile, do not have a good selectivity and a good capacity.

The invention claimed is:

1. A process for the purification of pentafluoroethane containing chloropentafluoroethane by extractive distillation, said process comprising the use of an extractant selected from dimethylformamide, dioxane, dimethylsulphoxide and diethylsulphoxide.

2. The process according to claim 1, in which the extractant is selected from dimethylsulphoxide and diethylsulphoxide.

3. The process according to claim 1, in which the distillation is carried out under a pressure ranging from atmospheric pressure to 20 bars.

4. The process according to claim 1, in which the pentafluoroethane/chloropentafluoroethane molar ratio before distillation ranges from 2 to 99.

5. The process according to claim 1, in which the pentafluoroethane/chloropentafluoroethane molar ratio after distillation ranges from 5 to 99999.

6. The process according to claim 1, in which the mixture containing pentafluoroethane and chloropentafluoroethane to be purified originates from the fluorination reaction of perchloroethylene or from an intermediate fluorination product of said perchloroethylene.

7. The process according to claim 6, in which the intermediate fluorination product of said perchloroethylene is selected from dichlorotrifluoroethane or chlorotetrafluoroethane.

8. The process according to claim 1, in which the mixture containing pentafluoroethane and chloropentafluoroethane to be purified originates from the hydrogenolysis reaction of chloropentafluoroethane.

\* \* \* \* \*